United States Patent [19]
Ligler et al.

[11] Patent Number: 5,354,654
[45] Date of Patent: Oct. 11, 1994

[54] LYOPHILIZED LIGAND-RECEPTOR COMPLEXES FOR ASSAYS AND SENSORS

[75] Inventors: Frances S. Ligler; James P. Whelan, both of Potomac, Md.

[73] Assignees: The United States of America as Represented by the Secretary of the Navy, Washington, D.C.; U.S. Drug Testing, Inc., Rancho Cucamonga, Calif.

[21] Appl. No.: 92,518

[22] Filed: Jul. 16, 1993

[51] Int. Cl.⁵ .............. G01N 33/543; G01N 33/566; G01N 33/569

[52] U.S. Cl. .......................... 435/5; 435/6; 435/7.1; 435/7.21; 435/7.22; 435/7.23; 435/7.24; 435/7.25; 435/7.3; 435/7.31; 435/7.32; 435/7.33; 435/7.34; 435/7.35; 435/7.36; 435/7.4; 435/7.8; 435/963; 436/500; 436/501; 436/506; 436/518; 436/513

[58] Field of Search .......................... 435/5–6, 435/7.1, 7.21–7.36, 7.4, 963, 7.8; 436/500, 501, 506, 513, 518, 508

[56] References Cited

U.S. PATENT DOCUMENTS

| | | | |
|---|---|---|---|
| 3,789,116 | 1/1974 | Kay | 436/547 |
| 4,256,725 | 3/1981 | Rutner et al. | 436/527 |
| 4,388,295 | 6/1983 | Cocola et al. | 436/531 |
| 4,461,829 | 7/1984 | Greenquist | 435/7 |
| 4,517,288 | 5/1985 | Giegel et al. | 435/7 |
| 4,692,331 | 9/1987 | Uemura et al. | 424/85 |
| 4,693,912 | 9/1987 | Spadaro et al. | 427/213.3 |
| 4,777,021 | 10/1988 | Wertz et al. | 422/101 |
| 4,786,606 | 11/1988 | Giegel et al. | 436/500 |
| 4,806,343 | 2/1989 | Carpenter et al. | 424/450 |
| 4,897,353 | 1/1990 | Carpenter et al. | 435/188 |
| 4,915,951 | 4/1990 | Baldeschwieler et al. | 424/450 |
| 4,931,361 | 6/1990 | Baldeschwieler et al. | 428/402.2 |
| 4,931,385 | 6/1990 | Block et al. | 435/7 |
| 4,963,362 | 10/1990 | Rahman | 424/450 |
| 5,071,598 | 12/1991 | Baldeschwieler | 264/4.3 |
| 5,089,181 | 2/1992 | Hauser et al. | 264/4.3 |
| 5,102,788 | 4/1992 | Cole | 435/7.9 |
| 5,183,740 | 2/1993 | Ligler et al. | 435/7.32 |
| 5,192,743 | 3/1993 | Hsu et al. | 514/8 |
| 5,200,399 | 4/1993 | Wettlaufer et al. | 514/23 |

OTHER PUBLICATIONS

Kusterbeck et al, "Antibody-Based Biosensor for Continuous Monitoring", in *Biosensor Technology*, R. P. Buck et al eds., Marcel Dekker, N.Y. pp. 345–350 (1990).

Kusterbeck et al, *Journal of Immunological Methods*, vol. 135, pp. 191–197 (1990).

Ligler et al, "Drug Detection Using the Flow Immunosensor", in *Biosensor Design and Application*, J. Findley et al, eds., American Chemical Society Press, pp. 73–80 (1992).

Ogert et al, *Analytical Letters*, vol. 25, pp. 1999–2019 (1992).

Wylie et al, *Analytical Biochemistry*, vol. 194, pp. 381–387 (1991).

Kusterbeck et al, "Detection of Small Molecules with a Flow Immunosensor", *Proceedings of Tech 2001*, San Jose Calif., NASA Conference Publication 3136, vol. 2, pp. 191–196.

Kirk-Othmer, *Encyclopedia of Chemical Technology*, 3rd. ed. vol. 8, pp. 109–110, Wiley, N.Y. (1979).

*Primary Examiner*—David Saunders
*Attorney, Agent, or Firm*—Oblon, Spivak, McClelland, Maier & Neustadt

[57] ABSTRACT

A dry reagent prepared by lyophilizing a labelled ligand-immobilized receptor complex or a labelled receptor-immobilized ligand complex is, on rehydration, useful for detecting analytes in samples in a variety of displacement assays.

22 Claims, 2 Drawing Sheets

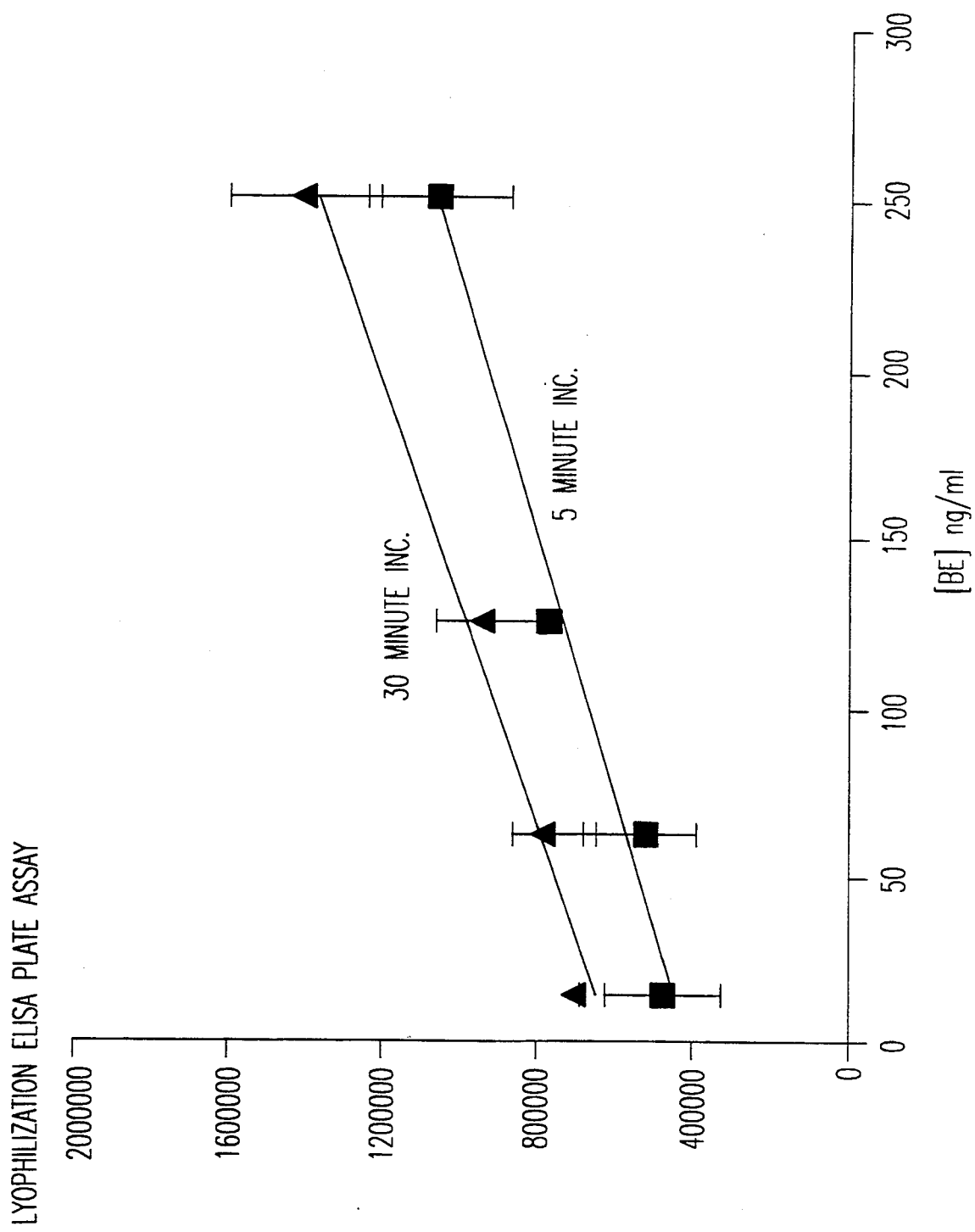

LYOPHILIZED LIGAND-RECEPTOR COMPLEXES FOR ASSAYS AND SENSORS

BACKGROUND OF THE INVENTION

1. Field of the Invention

The present invention relates to lyophilized ligand-receptor complexes, which are useful for assays and sensors, and processes for preparing such lyophilized ligand-receptor complexes. The present invention also relates to novel immunoassays utilizing such lyophilized ligand-receptor complexes, and kits containing such lyophilized ligand-receptor complexes.

2. Discussion of the Background

Ligand-receptor binding assays can be considered to be of four types: direct binding, sandwich assays, competition assays, and displacement assays. While the exact arrangement of ligands and receptors varies widely as does the type of readout system involved, the four types can be generally (but not exclusively) described as follows. In a direct binding assay, either the ligand or receptor is labelled, and there is a means of measuring the number of complexes formed. In a sandwich assay, the formation of a complex of at least three components (i.e. receptor-ligand-labelled receptor) is measured. In a competition assay, labelled ligand and unlabelled ligand compete for binding to the receptor, and either the bound or the free component is measured. In a displacement assay, the labelled ligand is prebound to the receptor, and a change in signal is measured as the unlabelled ligand displaces the bound labelled ligand from the receptor.

Displacement assays and flow immunosensors useful for carrying out displacement assays are described in: (1) Kusterbeck et al, "Antibody-Based Biosensor for Continuous Monitoring", in *Biosensor Technology*, R. P. Buck et al, eds., Marcel Dekker, N.Y. pp. 345–350 (1990); Kusterbeck et al, "A Continuous Flow Immunoassay for Rapid and Sensitive Detection of Small Molecules", *Journal of Immunological Methods,* vol. 135, pp. 191–197 (1990); Ligler et al, "Drug Detection Using the Flow Immunosensor", in *Biosensor Design and Application*, J. Findley et al, eds., American Chemical Society Press, pp. 73–80 (1992); and Ogert et al, "Detection of Cocaine Using the Flow Immunosensor", *Analytical Letters*, vol. 25, pp. 1999–2019 (1992), all of which are incorporated herein by reference. Displacement assays and flow immunosensors are also described in U.S. Pat. No. 5,183,740, which is also incorporated herein by reference. The displacement immunoassay, unlike most of the competitive immunoassays used to detect small molecules, can generate a positive signal with increasing antigen concentration.

In displacement assay systems, a critical feature of the assay is washing to remove unbound labelled ligand prior to the addition of the unlabelled ligand. When the amount of displaced labelled antigen is the "signal", any labelled molecule present in the system but not initially bound by the receptor is considered background and decreases the sensitivity of the assay.

Substrates are typically prepared for displacement assays by first immobilizing the receptor (or ligand) and then saturating the receptor binding sites with excess labelled ligand (or receptor). Immobilized receptors are typically stored in saline buffer with excess labelled ligands for long periods (over 1 year) prior to use. Since the labelled ligand is in excess, the complex does not dissociate. However, washing is required to remove the excess labelled antigen at the time of use. Since the washing must be performed just prior to the use of the immobilized receptor-ligand conjugate, such washings would typically be performed by the user, rather than the manufacturer. Thus, it is required that the user have sufficient skills to perform the washing step and that these washings be performed uniformly and thoroughly in order to achieve good results with the assay. It would be desirable if the washing step could be carried out by the manufacturer to insure that it is performed correctly. However, if the washing step is carried out too far in advance of use, it is possible for some of the bound labelled ligand (receptor) to dissociate from the immobilized receptor (ligand), which would result in a loss of sensitivity. In addition, long-term storage of many immobilized ligand-receptor complexes require storage in a refrigerator at temperatures below 5° C., a requirement which is met with difficulty in some areas of the world or when the assay is performed under field conditions.

U.S. Pat. No. 3,789,116 discloses a lyophilized labelled antibody reagent which contains a non-reducing polysaccharide, normal serum, and a labelled antibody. However, the reagent of this patent is not suitable for use in a displacement assay, because the labelled antibody (receptor) is not bound to an immobilized antigen or hapten (ligand).

U.S. Pat. No. 4,461,829 describes a homogeneous specific binding assay element which is prepared by a process involving: (a) incorporating a carrier with a reagent reactive with a label conjugate in a first liquid; (b) subjecting the carrier of (a) to conditions effective to reversibly suspend or reduce the activity of the reagent therein; (c) incorporating the carrier of (b) with the label conjugate; (d) subjecting the carrier of (c) to a temperature effective to freeze the regent reactive with the label conjugate and the label conjugate; and (e) lyophilizing the reagent and label conjugate in the carrier of (d). Again, the binding assay element of this patent is not suitable for use in a displacement assay, because the "label conjugate" (labelled ligand) is not bound to the "reagent" (receptor). In fact, the process is designed to insure that the binding of reactive reagent and labelled conjugate cannot occur prior to rehydration.

U.S. Pat. No. 4,692,331 discloses a dry γ-globulin preparation prepared by lyophilizing a solution of purified γ-globulin fraction and glucose. For obvious reasons, this preparation is also not usable in a displacement assay. First, the antibody is not immobilized, and second, the antibody is not bound to a labelled antigen or hapten.

U.S. Pat. No. 4,693,912 teaches a method of lyophilizing reagent-coated latex particles. Specifically, a reagent-coated particle, such as an antigen or antibody immobilized on a latex bead, is combined with a cryoprotective agent, and the mixture is lyophilized. Once again, the disclosed preparation is unsuitable for a displacement assay, because the immobilized reagent (ligand or receptor) is not bound with a labelled binding partner (labelled ligand or labelled receptor).

U.S. Pat. No. 5,102,788 discloses an immunoassay which utilizes a lyophilized reactant mixture. The reactant mixture includes antibody-gold sol particle conjugates, antibody latex particle conjugates, polyethylene glycol, p-isooctylphenyl ether detergent and a sugar such as dextrose or trehalose. As in the above-described preparations, the antibody is not bound to a labelled antigen or hapten, and thus, these preparations are also unsuitable for use in a displacement assay.

Thus, there remains a need for immobilized ligand-receptor complexes which are suitable for use in a displacement assay and do not require washing immediately prior to use and are suitable for long-term storage at ambient temperatures. There also remains a need for a process for preparing such ligand-receptor complexes.

SUMMARY OF THE INVENTION

Accordingly, it is one object of the present invention to provide novel ligand-receptor complexes which are suitable for use in a displacement assay.

It is another object of the present invention to provide novel ligand-receptor complexes which are suitable for use in a displacement assay and do not require washing prior to use.

It is another object of the present invention to provide novel ligand-receptor complexes which are suitable for use in a displacement assay and may be stored for extended periods of time at ambient temperatures.

It is another object of the present invention to provide processes for preparing such ligand-receptor complexes.

It is another object of the present invention to provide a simplified displacement assay which does not require washing of the ligand-receptor complex immediately prior to use.

It is another object of the present invention to provide kits which can be utilized to carry out such simplified displacement assays.

These and other objects, which will become apparent during the course of the following detailed description, have been achieved by the inventor's discovery that a ligand-receptor complex prepared by a process involving:

(i) binding a labelled ligand or a labelled receptor to an immobilized receptor or an immobilized ligand, to obtain an immobilized ligand-receptor complex;

(ii) washing said immobilized ligand-receptor complex to remove any excess labelled ligand or any excess labelled receptor, to obtain a washed immobilized ligand-receptor complex; and (iii) lyophilizing said washed immobilized ligand-receptor complex, to obtain a lyophilized immobilized ligand-receptor complex, is useful in displacement assays, does not require washing immediately prior to use, and is suitable for long term storage at ambient temperatures.

Prior to the present invention, whether or not a ligand-receptor complex having equilibrium binding constant, K, of $10^5$ to $10^9$ would dissociate during a lyophilization and rehydration cycle was unknown. If the immobilized receptor-labelled ligand complex could be washed prior to lyophilization, no washing step would be required of the operator at the time the assay or biosensor analysis was performed. However, the labelled ligand would not be in excess at the time of rehydration, and if it dissociated from the receptor, it would be not rebound in sufficient proportion to perform the displacement assay. Furthermore all dissociated labelled ligand would contribute the background in the assay.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2 shows the results of an embodiment of the present assay carried out in 96-well microtitre plate, ■ 5 minute incubation; ▲ 30 minute incubation).

DETAILED DESCRIPTION OF THE PREFERRED EMBODIMENTS

Figure 1:
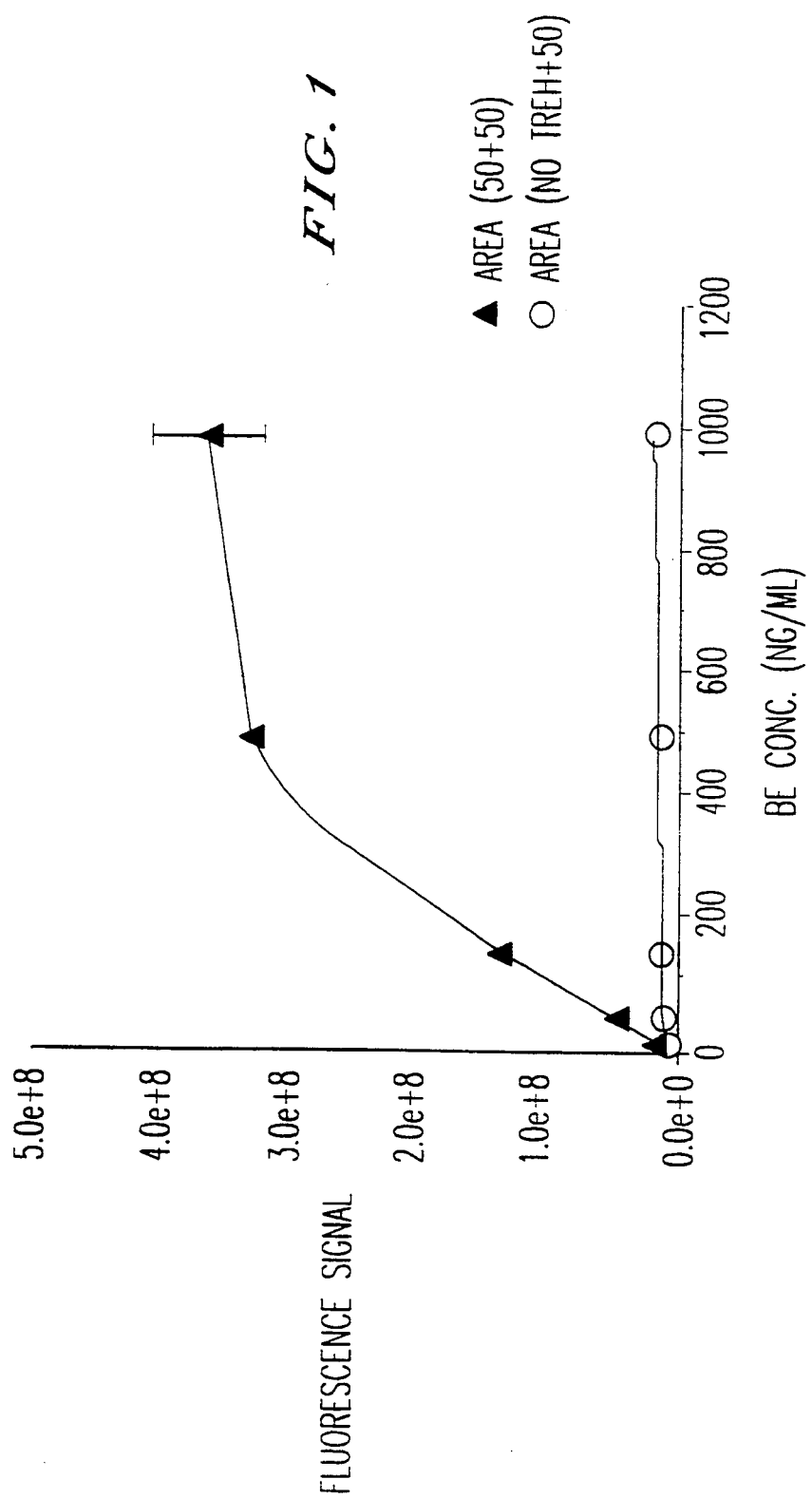
FIG. 1 depicts the relationship between the fluorescence signal and the concentration of applied antigen (BE) in an assay in which trehalose is present in the lyophilized ligand-receptor complex (▲) and in an assay in which no trehalose is present in the lyophilized ligand-receptor complex (O)

Thus, in a first embodiment, the present invention provides a method for preparing a reagent which is useful in displacement assays. In particular, the present invention provides a method for preparing lyophilized ligand-receptor complexes by (i) binding a labelled ligand or a labelled receptor to an immobilized receptor or an immobilized ligand, to obtain an immobilized ligand-receptor complex;

(ii) washing said immobilized ligand-receptor complex to remove any excess labelled ligand or any excess labelled receptor, to obtain a washed immobilized ligand-receptor complex; and (iii) lyophilizing said washed immobilized ligand-receptor complex, to obtain a lyophilized immobilized ligand-receptor complex, In the first step, a labelled ligand or a labelled receptor is bound to an immobilized receptor or an immobilized ligand. When an immobilized receptor is used, then it will be bound to a complementary ligand which has been labelled. On the other hand, when an immobilized ligand is used, then it will be bound to a complementary receptor which has been labelled. By the descriptor "complementary" it is meant that the particular ligand-receptor pair is capable of specific binding to one another.

Accordingly, the choice of immobilized receptor or immobilized ligand will depend on the identity of the labelled ligand or labelled receptor. Furthermore, the choice of the labelled ligand or the labelled receptor will depend on the identity of the analyte being detected. Thus, the choice of the immobilized receptor or immobilized ligand will ultimately depend on the identity of the analyte being detected. Quite simply, the labelled ligand-immobilized receptor pair or the labelled receptor-immobilized ligand pair must be chosen such that detectable quantities of either the labelled ligand or labelled receptor will be displaced from its respective binding partner when contacted with a sample containing an analyte in an amount corresponding to a positive test under the conditions of the assay. This means that analyte will also bind specifically to the immobilized receptor or immobilized ligand. As a corollary, the analyte may itself be either a ligand or a receptor.

As explained more fully below, the lyophilized ligand-receptor complexes of the present invention may be used in various types of assays, including those representative of equilibrium conditions and those of steady state conditions. Furthermore, these assays may be used to detect analytes having a wide range of concentrations in the samples. Accordingly, labelled ligand-immobilized receptor and labelled receptor-immobilized ligand pairs having a wide range of ligand-receptor affinities are suitable. Generally speaking, the strength of the ligand-receptor binding may be described by the equilibrium binding constant (K) for the equilibrium between free ligand and free receptor, on the one hand, and the bound ligand-receptor pair, on the other:

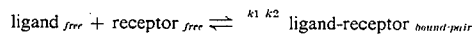

$$K = \frac{[\text{ligand-receptor}_{bound\text{-}pair}]}{[\text{ligand}_{free}][\text{receptor}_{free}]} = \frac{k_1}{k_2}$$

Depending on the type of assay in which the lyophilized ligand-receptor complex is to be used, the labelled ligand-immobilized receptor or labelled receptor-immobilized ligand pair typically have a K of from $10^4$ to $10^{12}$. In assays in which the signal detected arises from the labelled ligand or labelled receptor displaced from the immobilized binding partner, such as those utilizing a flow immunosensor, the K is more preferably $10^5$ to $10^9$. In assays in which the signal detected arises from the labelled ligand or labelled receptor which remains bound to the immobilized binding partner after incubation with the sample, such as those utilizing a microtitre plate, the K is more preferably $10^4$ to $10^8$. However, one of skill in the art will recognized that by varying the incubation time with and/or flow rate of the analyte-containing sample or the immobilization support and or method of immobilization, it is possible for good results to be obtained for ligand-receptor pairs having a K outside these ranges.

In general, the ligand-receptor pair may comprise any types of molecules capable of specific binding. Examples of such types of molecule pairs include: (1) antibody-antigen or hapten; (2) cell-surface receptor-hormone, cytokine, drug, or antibiotic; (3) lectin-carbohydrate (including glycoprotein and glycolipid); (4) DNA binding protein-DNA; (5) metal-metal chelators (including proteins, synthetic peptides, crown ethers, porphyrins, etc.); (6) enzyme-substrate; (7) nucleotide binding protein-nucleotide; (8) hapten-random or genetically engineered binding molecule (e.g., randomly generated phage polypeptide); etc. Especially good results have been achieved using antibody-antigen or hapten pairs as the receptor-ligand pair. The use of antibody-antigen or hapten pairs as the receptor-ligand pair is especially convenient due, in part, to the large variety of commercially available monoclonal antibodies which are specific for a large number of antigens and haptens.

An extensive list of antibodies applicable for use in the present invention are commercially available or can be made from descriptions of methods of preparation available in literature. Linscott's Directory provides the most complete single listing of commercially available antibodies ("Linscott's Directory", 40 Glen Drive, Mill Valley, Calif. 94941), and this reference is incorporated herein by reference. Any antibody described in the literature may be employed or adapted to the method of this invention.

As noted above, the choice of the labelled ligand-immobilized receptor or labelled receptor-immobilized ligand pair will ultimately depend on the analyte which is to be detected. Examples of analytes which may be assayed according to the present invention include biomolecules assayed in clinical tests; drugs of abuse; therapeutic drugs; environmental pollutants; substrates, contaminants, and products of industrial processes; explosives; and biological warfare agents.

Examples of biomolecules which are assayed in clinical tests include acetylcholine receptor antibody, adenovirus antigens, antibodies against adenovirus, aldosterone, acid phosphatase, alpha-1 fetoprotein, angiotensin converting enzyme, antiDNA antibody, antimitochondrial antibody, beta-2 microglobulin, cardiac enzymes (including creatine kinase isoenzymes, lactate dehydrogenase isoenzymes), complement components (including $C_1$, $C_{1q}$, $C_3$), chlamydia antigens, antibodies against chlamydia, cortisol, C-peptide, cyclic AMP, erthyropoietin, estradiol, ferritin, folic acid, follicle stimulating hormone, gastrin, glucagon, growth hormone, histocompatibility antigens, blood group antigens A and B, haptoglobin, antibodies against hepatitis A and B, hepatitis A and B antigens, antibodies against herpes, herpes antigens, human chorionic gonadotropin, HIV antigens, antibodies against HIV, antibodies against insulin, insulin, IgA, IgD, IgE, IgG, IgM, $H.$ influenza antigen, antibodies against the $H.$ influenza virus, intrinsic factor antibody, Borrelia burgdorferi antigens, antibodies against Borrelia burgdorferi, luteinizing hormone, metyrapone, myoglobin, neuron-specific-enolase, p24, pancreatic polypeptide, parathyroid hormone, placental lactogen, progesterone, prolactin, prostate specific antigen, rotavirus antigens, antibodies against rotavirus, antibodies against rubella, salmonella, serotonin, somatomedin-C, $T_3$, $T_4$, testosterone, thyroglobulin, thyroid stimulating hormone, thyroxine, thyroxine binding globulin, transferrin, tri-iodothyronine, vasoactive intestinal polypeptide, vitamins $B_6$ and $B_{12}$, staphylococcus antigens, antibodies against staphylococcus, enterotoxins, ricin, endotoxin, botulism toxin, and venoms (toad, wasp, spider, snake, fish, etc. ).

Examples of drugs of abuse include amphetamine, methamphetamine, phenobarbital, cocaine, methadone, methaqualone, opiates (morphine, heroin), tetrahydrocannabinol (THC), phencyclidine (PCP), lysergic acid diethylamide (LSD), annabolic steroids, and phenylbutazone.

Examples of therapeutic drugs include amikacin, azidothymidine, benzodiazepines (diazepam and chlordiazepoxide), carbamazine, chloramphenicol, cyclosporine, digitoxin, digoxin, ethosuximide, gentamicin, imipramine, lidocaine, phenytoin, primidone, procainamide, propoxyphene, propranolol, quinidine, theophylline, tobramycin, valproic acid.

Examples of suitable explosives include trinitrotoluene (TNT), cyclonite (RDX), pentaerythritol tetranitrate (PETN), picric acid, and nitroglycerin.

Examples of suitable environmental pollutants include herbicides (alachlor, atrazine, etc.), insecticides (e.g. DDT), polychlorinated biphenyls (PCBs), polyaromatic hydrocarbons (PAHs), and heavy metals (Hg, Pb, Cd, etc.).

Examples of substrates, contaminants, and products in industrial processes include, e.g., salmonella in foods and beverages; glucose and/or contaminating bacteria in fermentation processes; and endotoxin in pharmaceutical preparation processes.

Examples of biological warfare agents include enterotoxin, ricin, botulism toxin, F1 antigen of $Y.$ pestis, lethal factor or PA antigen from $B.$ anthracis, mycotoxins, and venoms.

It should be understood that in some cases the analyte actually detected will be a metabolite of one of the analytes listed above. This may be the case when a sample of biological origin is being assayed for a drug. For example, in the case of cocaine when testing urine, it is appropriate to detect the metabolite, benzoylecgonine. In such cases, the skilled artisan will be readily able to select an appropriate ligand-receptor pair.

Inspection of the above-given enumeration of suitable analytes reveals that in some instances the analyte itself is an antibody or other type of receptor. In these cases it is possible to utilize either: (1) a labelled ligand-immobilized receptor pair, in which the labelled ligand is a binding analog of the analyte and the immobilized receptor is, e.g., an antibody which binds specifically to both the analyte and the labelled ligand; or (2) a labelled receptor-immobilized ligand pair, in which the labelled receptor is a binding analog of the analyte and the immobilized ligand is, e.g., a hapten or antigen (in the case of an antibody analyte) which binds specifically to both the analyte and the labelled receptor. It is preferred to utilize a labelled ligand-immobilized receptor pair in which the labelled ligand is a binding analog of the analyte and the immobilized receptor is an antibody which binds specifically to both the analyte and the labelled ligand, in those cases when such an antibody is available.

The labelled ligand or labelled receptor may be the identical molecule as the analyte, with the exception of having a label covalently bound thereto. Alternatively, the labelled ligand or labelled receptor may be structurally distinct from the analyte, so long as it and the analyte both bind specifically to the immobilized receptor or immobilized ligand. Examples of labelled ligands or labelled receptors which are structurally distinct from the analyte include a labelled antibody fragment when the analyte is an antibody. In addition, labelled dinitrophenol can be used as the labelled ligand in an assay for dinitrophenol, TNT, or mixtures thereof. Similarly, antibody against benzoylecgonine can recognize both benzoylecgonine and cocaine.

The preparation of the labelled ligand or labelled receptor may be carried out by means of convention methods well known in the art. The label itself may suitably be a fluorophore, a chromophore, a radiolabel, a metal colloid, an enzyme, or a chemiluminescent or bioluminescent molecule. Suitable fluorophores and chromophores are disclosed in R. P. Haugland, *Molecular Probes, Handbook of Fluorescent Probes and Research Chemicals,* 5th Ed., Molecular Probes, Inc., Eugene, Oreg., 1992, which is incorporated herein by reference. Examples of preferred fluorophores include fluorescein, rodamine, and sulfoindocyanine dye Cy5 (Mujumdar, R. B., et al, *Bioconjugate Chemistry,* vol. 4, p. 105 (1992). Preferred radiolabels include $^{125}I$, $^{32}P$, $^{14}C$ and $^{3}H$. Preferred enzymes include horseradish peroxidase, alkaline phosphatase, glucose oxidase, and urease.

Typically, the label is attached to the ligand or receptor by means of a crosslinking agent. Examples of suitable crosslinking agents are disclosed in *Pierce Catalog,* Pierce, Rockford, Ill. 1993; and S. S. Wong, *Chemistry of Protein Conjugation and Crosslinking,* CRC Press, Boca Raton, Fla., (1993), 340 pages, which are incorporated herein by reference. The methods utilized to form the bonds between the receptor or ligand and the crosslinking agent and between the label and the crosslinking agent are in themselves well known to those of skill in the art.

Although the above-given discussion has pointed out the use of crosslinking agents for binding the label to either to the ligand or receptor to be labelled, it should be understood that in some cases it is possible to attach the label directly to the ligand or receptor. For example, many fluorophores include succinimide groups which can be attached directly to amino groups on ligands and receptors.

The support for the immobilized receptor or immobilized ligand may be composed of glass, silicon, quartz, paper, nitrocellulose, or polymers, such as latex, plastic, and hydrogels and may be in the form of a slide, beads, a membrane, tubing, etc. In some cases, it is preferred that the support on which the immobilized receptor or ligand is immobilized is a side wall of a reaction vessel in which an assay is carried out, such as a glass or plastic tube or the well of a microtitre plate. The immobilization of the ligand or receptor to be immobilized on the support may be carried out by means of conventional methods which are well known to those of skill in the art. The term immobilization is meant to include both covalent linkage and physical adsorption. Such methods are disclosed in *Protein Immobilization Fundamentals and Applications,* R. M. Taylor, Ed., M. Dekker, N.Y., 1991, 377 pages; and Goldstein, L. et al, "Chemistry of Enzyme Immobilization" in *Immobilized Enzyme Principals,* L. G. Wingard, Jr., ed. , Academic Press, N.Y., pp. 23–126 (1976); which are incorporated herein by reference.

The formation of the labelled ligand-immobilized receptor or labelled receptor-immobilized ligand complex may be carried out by incubating the labelled ligand or labelled receptor with the immobilized receptor or immobilized ligand. When using an antibody-antigen or hapten pair as the ligand-receptor complex, this incubation is typically carried out in an aqueous medium such as a buffer, having a pH of 5 to 8.5, preferably 6 to 8. To maximize the sensitivity of the assay, it is preferred that all of the binding sites of the immobilized receptor or immobilized ligand be saturated with the labelled binding partner. Thus, the incubation is usually carried out using an excess of labelled ligand or labelled receptor as compared to the amount of immobilized receptor or immobilized ligand present in the incubation mixture, to ensure saturation of the immobilized receptor or immobilized ligand with labelled ligand or labelled receptor. Suitably, the labelled ligand or labelled receptor is present in an amount equal to 1 to 500, preferably 1 to 100, times the theoretical amount necessary to bind all the immobilized receptor or immobilized ligand in the incubation mixture. The incubation is suitably carried out at a temperature of 4° to 37° C. preferably 4° to 25° C., for a time of 2 min. to 24 hours, preferably 1 to 12 hours.

After the incubation is complete, the labelled ligand-immobilized receptor or labelled receptor-immobilized ligand complex is then washed to remove the excess, unbound labelled ligand or labelled receptor. The washing may be carried out by means of any conventional technique in which the liquid medium, which surrounds the labelled ligand-immobilized receptor or labelled receptor-immobilized ligand complex and which contains the excess labelled ligand or excess labelled receptor, is replaced with a liquid medium which does not contain labelled ligand or labelled receptor. Typically, this washing is carried out using the same types of aqueous buffers used in the incubation step.

The washing may be carried out in a stepwise fashion using an iterative process in which: (i) the labelled ligand-immobilized receptor or labelled receptor-immobilized ligand is separated (by, e.g., filtration, decantation, etc.) from the liquid medium used in the incubation; (ii) the separated labelled ligand-immobilized receptor or labelled receptor-immobilized ligand complex is then exposed and incubated in fresh liquid medium which does not contain any labelled ligand or labelled receptor; (iii) the labelled ligand-immobilized receptor or labelled receptor-immobilized complex is again separated from the liquid medium in step (ii); and (iv) steps (ii) and (iii) are repeated until the washing is complete. Alternatively, the washing may be carried out in a continuous fashion. For example, the labelled ligand-immobilized receptor or labelled receptor-immobilized ligand complex may be packed in a column, and the column may be flushed with a liquid medium which does not contain labelled ligand or labelled receptor. It is possible to monitor the washing, e.g., by measuring the amount of signal present in the liquid medium which is separated form the ligand-receptor complex in step (iii) of the iterative process described above or the liquid medium exiting form the column in the continuous process described above.

After the washing step is complete, the washed labelled ligand-immobilized receptor or labelled receptor-immobilized ligand is then lyophilized. The lyophilization may be carried out using any conventional lyophilization apparatus. Techniques and apparatus for lyophilization are disclosed in Flosdorf, E. W., *Freeze-Drying*, Reinhold Publishing Corp., N.Y. (1949); Harris, R. J. C., ed., *Biological Applications of Freezing and Drying*, Academic Press, N.Y. (1954); Parkes and Smith, eds., *Recent Research in Freezing and Drying*, Blackwell Oxford (1960); Meryman, H. T., "Freeze-Drying", in *Cryobiolog*, Meryman, , ed., Academic Press, N.Y. (1966); and Kirk-Othmer, *Encyclopedia of Chemical Technology*, 3rd ed., vol. 8, pp. 109–110, Wiley, N.Y. (1979), all of which are incorporated herein by reference.

In some embodiments, it is preferred that the lyophilization of the labelled ligand-immobilized receptor or labelled receptor-immobilized ligand complex be carried out in the presence of a cryoprotectant. Suitable cryoprotectants include disaccharides, polysaccharides, glycerol, proteins, surfactants, serum, buffer formulations previously reported for lyophilization of proteins, polyethylene glycol and dimethyl sulfoxide. Such cryoprotectants and lyophilization using such cryoprotectants are disclosed in U.S. Pat. Nos. 5,200,399, 5,192,743, 5,089,181, 5,071,598, 4,963,362, 4,931,361, 4,915,951, 4,897,353, and 4,806,343, which are incorporated herein by reference. Typically, the cryoprotectant will be mixed with the sample containing the liquid medium and labelled ligand-immobilized receptor or labelled receptor-immobilized ligand complex prior to the lyophilization. Although the exact amount of cryoprotectant will depend, in part, on the identity of the cryoprotectant and the sensitivity of the particular ligand-receptor pair, the cryoprotectant is usually present in an amount sufficient to replace the water molecules associated with the ligand-receptor complex. The preferred amount of cryoprotectant may be experimentally determined by testing a range of concentrations for a given system and determining which concentration gives the best results, with regard to the activity of the rehydrated system. The preferred cryoprotectants are trehalose, glucose and lysine.

The above-described process yields a dry reagent comprising a labelled ligand or a labelled receptor bound to complementary receptor or a complementary ligand, in which the complementary receptor or complementary ligand is immobilized on a solid support.

The use of the dry reagents of the present invention will be described more fully below with regard to assays carried out in flow immunosensors or microtitre plates. However, it is to be understood that the dry reagents of the present invention may be utilized in other types of assays and apparatus as well.

As noted above, the apparatus and conditions for carrying out an assay with a flow immunosensor are described in U.S. Pat. No. 5,183,740, which is incorporated herein by reference. In such assays, the sample containing the analyte is typically passed through a column containing a labelled ligand-immobilized receptor complex and the amount of labelled ligand displaced by the analyte is detected in the liquid phase exiting the column.

Specifically, U.S. Pat. No. 5,183,740 discloses, in part, that:

In the method of the invention, the displacement of the labelled antigen occurs under non-equilibrium conditions in seconds. It is hypothesized that the mechanics of the reaction do not follow those described for immobilized antigen/antigen complexes in static systems. The detection method is based on the displacement of a pre-bound labelled complex with a similar or equivalent antigenic site and not solely on the binding of antigen to the column. The displacement reaction may not reflect simple equilibrium binding of the prior art as the target molecule is not allowed sufficient time in the vicinity of the antibody/labelled-antigen complex to allow equilibration or occur. The method and immunosensor of this invention rely on the dissociation of antigen from the antibody binding site instead of the association of antibody and antigen.

The goal of the method and immunosensor, also referred to as a flow immunosensor, of this invention is to provide and almost instantaneous indication of the present of a target by continuously monitoring an environment for the presence of a specific chemical or biological species (antigen). The method and immunosensor can be used to monitor for more than one chemical or species at a time.

The invention is not limited to situations where the flow of suspect material is expected on a continuous basis. The concept of the invention lies in being able to monitor an activity in real time instead of removing a sample from the going "stream" and analyzing it separately. Of course, the method and device of this invention can be used to analyze or check a specific sample or multiple discrete samples on a sample-by-sample basis by injecting the samples onto the liquid flow stream. In other words, single or multiple samples can be processed by the method of this invention in the immunosensor of this invention to obtain rapid analyses of the samples.

Generally, the method of this invention involves flowing a stream of liquid from a sample receiving means through an exchange area which contains a labelled antigen bound to an immobilized antibody specific for the target. The antigen and antibody are such that they do not react with the flowing liquid. Following the pass through the exchange area, the liquid passes through a detection apparatus capable of detecting the label on the labelled antigen if any.

To operate the method, a sample is injected into the liquid flow stream and passes through the exchange area. Alternatively, the sample can be dispersed in a volume of liquid and this volume of liquid introduced into the flowing stream as the sample. In yet another alternative embodiment, the sample is dispersed in a volume of liquid and the volume of liquid is used as the liquid flow stream. If the sample contains a target, the target will displace the labelled antigen which will flow in the liquid stream through the detection apparatus where it will be detected. The liquid, with or without a sample, flows from the detection apparatus to a disposal or recovery area where it is appropriately dealt with.

The liquids used in this invention are water, buffers, and aqueous sample diluents. Preferred liquids are buffers such as phosphate-buffered saline, borate-buffered saline, TRIS-saline, Alseiver's, and Ringer's. The buffers for biological uses are described generally in this booklet "Buffers", edited by Donald Guoffrey, published by American Hoechst Corporation La Jolla, Calif. (1983). The exact liquid is not critical to the invention as long as the liquid is a solvent for the target and reagents used in the process and as long as the liquid does not chemically react with the target or reagents of the method or the components of the immunosensor apparatus.

The flow rate of the liquid stream in the method of this invention should be between 0.1 and 2.0 milliliters per minute, preferably between 0.3 and 0.8 milliliters per minute. The optimum flow rate is such that the residence time of the target on the exchanger is sufficient to generate displacement of measurable quantities of labelled antigen in the shortest possible time.

A major advantage of this method is that reagents other than the flowing fluid are not exhausted unless a positive result, which can be referred to as a "hit" is detected. With the proper design of the apparatus to automate this method, the buffer can be recycled until there is a "hit". Following a "hit" the exchange area can be replaced or regenerated.

To regenerate the exchange area, fluid containing and excess of the labelled antigen is introduced into the exchange area. The labelled antigen will exchange with the unlabelled target and saturate the antibody binding sites. Because the regeneration is an equilibrium exchange reaction, the concentration of the labelled antigen in the buffer should be as high as possible and the dwell time of the labelled antigen in the exchange area should be as long as possible to favor a complete exchange.

The principal parts of the flow immunosensor are (1) the column and support medium containing immobilized antibodies for specific biochemical recognition of the antigen of interest, (2) the labelled antigen complexes, and (3) the flow system monitor or detector. Of course, ancillary equipment such as connecting tubing, a pump, and valves, is needed to make a fully operable immunosensor apparatus, but the means of connecting such ancillary equipment is done in the usual manner once the principles of this invention are seen. The specific components must be made of materials which will not interact or contaminate the reagents of the method of this invention. As needed and in the manner known in the art for such devices, computer hardware and software can be added to automate the system.

To utilize the present dry reagent in such an apparatus it is only necessary to rehydrate the dry reagent before passing the sample through the column. Further, the dry reagent may be rehydrated either before or after packing the column. In fact, it is also possible to carry out the washing and lyophilization steps after the column has been packed. Thus, in a preferred embodiment the column is provided to the consumer already containing the lyophilized ligand-receptor complex. To maximize the sensitivity of this type of assay, the dry reagent in the column should be rehydrated before passing the sample through the column. The dry reagent may be rehydrated with water or an aqueous buffer.

Alternatively, the present dry reagent may be used in an assay in which the amount of labelled ligand or labelled receptor remaining bound to the immobilized binding partner is measured. A preferred embodiment of such an assay is carried out using a microtitre plate in which the wells of the plate contain the present dry reagent. In a particularly preferred embodiment, the microtitre plate wells are the solid support on which the immobilized receptor or immobilized ligand are immobilized. In this embodiment, the sample may be added directly to the wells of the plate and then incubated. The time of incubation can be chosen for convenience, but is usually 1 to 60 min. At long incubation times this assay approaches a system in which the competitive binding of the analyte and the labelled ligand or labelled receptor to the immobilized binding partner is at equilibrium. An advantageous feature of this embodiment is that the sample may also serve as the liquid medium for rehydrating the dry reagent.

After the incubation is complete, the liquid medium (i.e. sample) is removed from the wells and the amount of labelled ligand or labelled receptor remaining in the well is measured. Of course, it is also possible to measure the amount of labelled ligand or labelled receptor present in the liquid medium removed from the wells.

This embodiment may be carried out using any conventional microtitre plate and any conventional means for adding and removing liquid from the wells of the plate. Alternatively, it is possible to use a plate such as that described in U.S. Pat. No. 4,777,021, which is incorporated herein by reference. In this type of plate, the wells rest over a waste chamber connected to a vacuum means, and the bottom of each well is a membrane through which fluid can be drawn upon the application of vacuum. Thus, with this type of plate, the liquid may be removed by means of suction filtration.

Typically, microtitre plates contain 96 wells. This means that a single plate could be used for testing a serial dilution of many samples and also contain enough wells for internal standards.

The samples used in the present assays may be of any origin and may even include those which are originally solid or airborne, so long as they can be dissolved, suspended, or captured in a liquid medium suitable for use in the present assays. When the sample is of biological origin, fluids such as blood, serum, saliva, spinal fluid, urine, sweat, amniotic fluid, extracts thereof, etc. are suitable for testing. Examples of other types of samples include ground water, aerosols, fluids from air samplers (such as cyclones or impaction devices), liquid extracts of solids (dirt, food, tissues, etc.) fermentation broths, and waste streams from factories.

The detection of the signal generated by the label on the labelled ligand or labelled receptor which has either been displaced from or remains bound to the immobilized binding partner may be carried out by any conventional means. Of course, the selection of the detector will depend on the nature of the label.

The type of assays that can be performed as displacement assays include but are not limited to radioimmunoassays, enzyme-linked immunosorbant assays, fluorescence assays, biosensor-based assays (demonstrated using the flow immunosensor and the fiber optic biosensor), flow injection assays, "dip stick" tests, acoustic wave immunoassays, piezoelectric analyses, surface plasmon resonance assays, luminescent assays, and electrochemical analyses.

The present invention also provides novel kits which contain the present lyophilized, dry reagent for use in the present displacement assays. Such kits will contain a container means which contains the present lyophilized, dry reagent. The container means may be any suitable container, but will typically be a glass vial or jar, a plastic pack, etc. In some embodiments, the container means may be a foil or plastic pouch which contains the dry reagent immobilized on a microtitre plate. In other embodiments, the container means may be a plastic, glass, or metal tube which contains the dry reagent, and the tube may possess an inlet means at one end and an outlet means at the other end; this type of container means may be used as the column in a flow immunosensor and may itself be contained in a second container means.

The kit may further comprise a negative control sample. Such a negative control sample will contain either no analyte or a very low amount of analyte. The kit may also comprise a positive control sample, which will comprise, typically, an amount of analyte which is equal to or greater than the amount of analyte which is considered a positive result. The kit may also contain chemicals, such as buffers or diluents, and sample handling means, such as pipettes, reaction vials, vessels, tubes, or filters.

In addition, the kit may comprise written instructions on a separate paper, or any of the container means, or any other packaging. These instructions will usually set forth the conditions for carrying out the displacement assay, such as mixing ratios, amounts, incubation times, etc., and criteria for evaluating the results of the assay, including color charts.

The present invention significantly reduces both the time and the number of steps involved for an operator to perform a displacement immunoassay. The ability to lyophilize and rehydrate the receptor (or ligand) with the labelled ligand (or receptor), without dissociating the complex, is a new feature. The present invention means that the materials in a set of assays or kits can be prepared (in quantity) and stored until needed.

A critical part of the initial preparation of the materials is the washing away of the unbound labelled ligand prior to the lyophilization. Since the assay operator does not have to perform a wash step at the time of rehydration, his operation is faster and less complicated. Accordingly, the present assays are more amenable to automation and use in biosensors.

Furthermore, there is less variation in the background from unbound labelled ligand (or receptor) if materials for many assays are washed simultaneously than if the materials for each individual assay are washed separately.

As alluded to above, prior to the present invention, the skilled artisan would not have expected a ligand-receptor complex to remain intact after lyophilization and rehydration. As shown in Example 2, described below, rehydration with a liquid containing the analyte results in an increasing displacement of labelled antigen as the incubation time is increased. If the labelled ligand and immobilized receptor were dissociated in the lyophilized state, the opposite effect would have been observed.

Having generally described this invention, a further understanding can be obtained by reference to certain specific examples which are provided herein for purposes of illustration only and are not intended to be limiting unless otherwise specified.

EXAMPLES

EXAMPLE 1

PREPARATION OF LYOPHILIZED SOLID SUPPORT AND USE OF LYOPHILIZED BEADS IN A FLOW IMMUNOSENSOR

Lyophilization and Rehydration:

1) Transferred 1.0 ml of controlled pore glass beads (24.2 nm pore size), coated with anti-benzoylecgonine antibody, to 5 cc syringe with a frit.

2) Remove buffer from matrix with vacuum aspirator.

3) Apply benzoylecgonine-Cy5 (300-molar excess) solution directly to glass beads. Cy5 is a fluorescent dye sold by BDS and Research Organics. (Benzoylecgonine-Cy5 solution should be in PBS pH 7.3 with bed volume ratio proportional to matrix bed).

4) Tap syringe to evenly mix matrix with fluorescent antigen.

5) Saturate column with fluorophore overnight at 4° C.

6) Prepare appropriate concentrations of Trehalose-Phosphate buffers.
  A) 50 mM Trehalose +50 mM Phosphate pH 7.3
  B) No Trehalose +50 mM Phosphate pH 7.3

7) Drain column of excess benzoylecgonine-Cy5 by gravity. (Collect excess in 15 ml tube).

8) Apply 1.0 ml of PBS pH 7.3 of PBS pH 7.3 (3X) to column to wash excess. (Save all benzoylecgonine-Cy5 fractions collected).

9) Add 1.0 ml of PBS buffer to matrix.

10) Aliquot 100 ul glass beads into separate microcolumns.

11) Drain each column of buffer by gravity.

12) Add 0.5 ml of each phosphate with or without trehalose to respective columns.

13) Drain columns of buffers by gravity leaving minimal head volume.

14) Cap bottom and top of column.

15) Place columns in freezer ($-70°$ C.) for 10 minutes.

16) Remove columns from freezer. Replace top cap with slitted parafilm.

17) Place columns in lyophilization container for overnight freeze drying. (Cover container with foil to prevent photodegradation of dye).

18) Remove columns from lyophilizer and store desiccated.

19) Add between 0.3 ml and 1.0 ml PBS to rehydrate matrix.

20) Let matrix settle and remove supernatant.

21) Add 0.5 to 1.0 ml of PBS to matrix.

Assay:

22) Attach column to continuous flow system.

23) Introduce various concentrations of benzoylecgonine (BE) to the columns and measure displacement of benzoylecgonine-Cy5 from column.

24) The column lyophilized in the presence of trehalose gave results comparable to an unlyophilized column. In contrast, as shown by the results in FIG. 1, the column lyophilized without trehalose did not generate a displacement signal upon introduction of benzoylecgonine, indicating that the labelled antigen did not remain bound during lyophilization and rehydration in the absence of the cryoprotectant. In FIG. 1, the experiments using the columns prepared using buffer A in step 6) are represented by ▲, while the experiments using the columns prepared using buffer B are represented by O.

EXAMPLE 2

Lyophilization Elisa Plate Assay

The objective of this assay is to prepare immobilized antibodies that are pre-saturated with labeled antigens, washed and freeze-dried in a 96-well microtitre plate format and to demonstrate the use of such prepared plates in an immunoassay. These assay plates are used routinely in research and diagnostic tests and permit parallel processing of many samples (or parameters) at the same time.

Protocol

Plate Preparation:

Monoclonal antibody specific for cocaine metabolite (benzoylecgonine) is adsorbed in the wells of the assay plate at a concentration of 4 micrograms/ml overnight. The plates are washed of excess antibody and saturated with fluorescently-labeled cocaine metabolite (benzoylecgonine) at a concentration of 5 micromolar for 2 hours. The plates are then washed of excess dye and the wells are then filled with a solution of 50 millimolar phosphate buffer, pH 7.4, containing 50 millimolar trehalose. The plates are then quickly frozen in a dry ice/methanol solution and dehydrated in the shelf lyophilizer for 24 hours.

Assay:

Samples were added directly to the wells of the plate (in triplicate). Samples contained either no drug or drug (benzoylecgonine, BE) at concentrations between 15–250 nanograms/ml in PBS. The samples were incubated for either 5 or 30 minutes, aspirated out and injected through the Jasco Spectrofluorimeter. Signal areas were obtained from a Hewlett-Packard integrator attached to the fluorimeter. The results are shown in FIG. 2, in which the signals shown are after background (no drug) levels were subtracted. The 5 minute incubation experiment results are indicated by ■, and the 30 minute incubation experiment results are indicated by ▲. The error bars represent SEM.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by letters patent of the United States is:

1. A lyophilized ligand-receptor complex, prepared by a process comprising:
 (i) binding a labelled ligand or a labelled receptor to an immobilized receptor or an immobilized ligand, to obtain an immobilized ligand-receptor complex;
 (ii) washing said immobilized ligand-receptor complex to remove any excess labelled ligand or any excess labelled receptor, to obtain a washed immobilized ligand-receptor complex; and
 (iii) lyophilizing said washed immobilized ligand-receptor complex, to obtain a lyophilized immobilized ligand-receptor complex,
wherein said lyophilizing is carried out in the presence of a cryoprotectant.

2. The lyophilized ligand-receptor complex of claim 1, wherein step (i) is carried out by binding a labelled antigen or labelled hapten to an immobilized antibody and wherein said lyophilized immobilized ligand-receptor complex is a lyophilized labelled antigen-immobilized antibody complex or a lyophilized labelled hapten-immobilized antibody complex.

3. The lyophilized ligand-receptor complex of claim 1, wherein said cryoprotectant is selected from the group consisting of disaccharides, polysaccharides, glycerol, proteins, surfactants, serum, buffers, polyethylene glycol, and dimethyl sulfoxide.

4. The lyophilized ligand-receptor complex of claim 1, wherein said immobilized receptor or immobilized ligand is capable of specific binding to an analyte selected from the group consisting of acetylcholine receptor antibody, adenovirus antigens, antibodies against adenovirus, aldosterone, acid phosphatase, alpha-1 fetoprotein, angiotensin converting enzyme, antiDNA antibody, antimitochondrial antibody, beta-2 microglobulin, creatine kinase isoenzymes, lactate dehydrogenase isoenzymes, complement components, chlamydia antigens, antibodies against chlamydia, cortisol, C-peptide, cyclic AMP, erthyropoietin, estradiol, ferritin, folic acid, follicle stimulating hormone, gastrin, glucagon, growth hormone, histocompatibility antigens, blood group antigens A and B, haptoglobin, antibodies against hepatitis A and B, hepatitis A and B antigens, antibodies against herpes, herpes antigens, human chorionic gonadotropin, HIV antigens, antibodies against HIV, antibodies against insulin, insulin, IgA, IgD, IgE, IgG, IgM, H. influenza antigen, antibodies against the H. influenza virus, intrinsic factor antibody, Borrelia burgdorferi antigens, antibodies against Borrelia burgdoferi, luteinizing hormone, metyrapone, myoglobin, neuron-specific-enolase, p24, pancreatic polypeptide, parathyroid hormone, placental lactogen, progesterone, prolactin, prostate specific antigen, rotavirus antigens, antibodies against rotavirus, antibodies against rubella, salmonella, serotonin, somatomedin-C, $T_3$, $T_4$, testosterone, thyroglobulin, thyroid stimulating hormone, thyroxine, thyroxine binding globulin, transferrin, tri-iodothyronine, vasoactive intestinal polypeptide, vitamins $B_6$ and $B_{12}$, staphylococcus antigens, antibodies against staphylococcus, enterotoxins, ricin, endotoxin, botulism toxin, venoms, amphetamine, methamphetamine, phenobarbital, cocaine, methadone, methaqualone, opiates (morphine, heroin), tetrahydrocannabinol (THC), phencyclidine (PCP), lysergic acid diethylamide (LSD), annabolic steroids, phenyl-butazone, amikacin, azidothymidine, benzodiazepines (diazepam and chlordiazepoxide), carbamazine, chloramphenicol, cyclosporine, digitoxin, digoxin, ethosuximide, gentamicin, imipramine, lidocaine, phenytoin, primidone, procainamide, propoxyphene, propranolol, quinidine, theophylline, tobramycin, valproic acid, trinitrotoluene, cyclonite, pentaerythritol tetranitrate, picric acid, nitroglycerin, herbicides, insecticides, polychlorinated biphenyls, polyaromatic hydrocarbons, heavy metals, glucose, F1 antigen of Y pestis, lethal factor or PA antigen from B. anthracis, and mycotoxins.

5. A process for preparing a lyophilized ligand-receptor complex, comprising:
 (i) binding a labelled ligand or a labelled receptor to an immobilized receptor or an immobilized ligand, to obtain an immobilized ligand-receptor complex;

(ii) washing said immobilized ligand-receptor complex to remove any excess labelled ligand or any excess labelled receptor, to obtain a washed immobilized ligand-receptor complex; and (iii) lyophilizing said washed immobilized ligand-receptor complex, to obtain a lyophilized immobilized ligand-receptor complex, wherein said lyophilizing is carried out in the presence of a cryoprotectant.

6. The process of claim 5, wherein step (i) is carried out by binding a labelled antigen or labelled hapten to an immobilized antibody and wherein said lyophilized immobilized ligand-receptor complex is a lyophilized labelled antigen-immobilized antibody complex or a lyophilized labelled hapten-immobilized antibody complex.

7. The process of claim 5, wherein said cryoprotectant is selected from the group consisting of disaccharides, polysaccharides, glycerol, proteins, surfactants, serum, buffers, polyethylene glycol, and dimethyl sulfoxide.

8. The process of claim 5, wherein said immobilized receptor or immobilized ligand is capable of specific binding to an analyte selected from the group consisting of acetylcholine receptor antibody, adenovirus antigens, antibodies against adenovirus, aldosterone, acid phosphatase, alpha-1 fetoprotein, angiotensin converting enzyme, antiDNA antibody, antimitochondrial antibody, beta-2 microglobulin, creatine kinase isoenzymes, lactate dehydrogenase isoenzymes, complement components, chlamydia antigens, antibodies against chlamydia, cortisol, C-peptide, cyclic AMP, erthyropoietin, estradiol, ferritin, folic acid, follicle stimulating hormone, gastrin, glucagon, growth hormone, histocompatibility antigens, blood group antigens A and B, haptoglobin, antibodies against hepatitis A and B, hepatitis A and B antigens, antibodies against herpes, herpes antigens, human chorionic gonadotropin, HIV antigens, antibodies against HIV, antibodies against insulin, insulin, IgA, IgD, IgE, IgG, IgM, *H. influenza* antigen, antibodies against the *H. influenza* virus, intrinsic factor antibody, *Borrelia burgdorferi* antigens, antibodies against *Borrelia burgdoferi*, luteinizing hormone, metyrapone, myoglobin, neuron-specific-enolase, p24, pancreatic polypeptide, parathyroid hormone, placental lactogen, progesterone, prolactin, prostate specific antigen, rotavirus antigens, antibodies against rotavirus, antibodies against rubella, salmonella, serotonin, somatomedin-C, T$_3$, T$_4$, testosterone, thyroglobulin, thyroid stimulating hormone, thyroxine, thyroxine binding globulin, transferrin, tri-iodothyronine, vasoactive intestinal polypeptide, vitamins B$_6$ and B$_{12}$, staphylococcus antigens, antibodies against staphylococcus, enterotoxins, ricin, endotoxin, botulism toxin, venoms, amphetamine, methamphetamine, phenobarbital, cocaine, methadone, methaqualone, opiates (morphine, heroin), tetrahydrocannabinol (THC), phencyclidine (PCP), lysergic acid diethylamide (LSD), annabolic steroids, phenyl-butazone, amikacin, azidothymidine, benzodiazepines (diazepam and chlordiazepoxide), carbamazine, chloramphenicol, cyclosporine, digitoxin, digoxin, ethosuximide, gentamicin, imipramine, lidocaine, phenytoin, primidone, procainamide, propoxyphene, propranolol, quinidine, theophylline, tobramycin, valproic acid, trinitrotoluene, cyclonite, pentaerythritol tetranitrate, picric acid, nitroglycerin, herbicides, insecticides, polychlorinated biphenyls, polyaromatic hydrocarbons, heavy metals, glucose, F1 antigen of *Y pestis*, lethal factor or PA-antigen from *B. anthracis*, and mycotoxins.

9. A lyophilized, dry reagent, comprising: (a) a labeled ligand or labeled receptor bound to (b) a complementary receptor or a complementary ligand, wherein said complementary receptor or complementary ligand is immobilized on a solid support, wherein said lyophilized, dry reagent is prepared by lyophilizing in the presence of a cryoprotectant.

10. The dry reagent of claim 9, comprising a labelled antigen or labelled hapten bound to a complementary antibody, wherein said complementary antibody is immobilized on a solid support.

11. The lyophilized, dry reagent of claim 9, wherein said immobilized receptor or immobilized ligand is capable of specific binding to an analyte selected from the group consisting of acetylcholine receptor antibody, adenovirus antigens, antibodies against adenovirus, aldosterone, acid phosphatase, alpha-1 fetoprotein, angiotensin converting enzyme, antiDNA antibody, antimitochondrial antibody, beta-2 microglobulin, creatine kinase isoenzymes, lactate dehydrogenase isoenzymes, complement components, chlamydia antigens, antibodies against chlamydia, cortisol, C-peptide, cyclic AMP, erthyropoietin, estradiol, ferritin, folic acid, follicle stimulating hormone, gastrin, glucagon, growth hormone, histocompatibility antigens, blood group antigens A and B, haptoglobin, antibodies against hepatitis A and B, hepatitis A and B antigens, antibodies against herpes, herpes antigens, human chorionic gonadotropin, HIV antigens, antibodies against HIV, antibodies against insulin, insulin, IgA, IgD, IgE, IgG, IgM, *H. influenza* antigen, antibodies against the *H. influenza* virus, intrinsic factor antibody, *Borrelia burgdorferi* antigens, antibodies against *Borrelia burgdoferi*, luteinizing hormone, metyrapone, myoglobin, neuron-specific-enolase, p24, pancreatic polypeptide, parathyroid hormone, placental lactogen, progesterone, prolactin, prostate specific antigen, rotavirus antigens, antibodies against rotavirus, antibodies against rubella, salmonella, serotonin, somatomedin-C, T$_3$, T$_4$, testosterone, thyroglobulin, thyroid stimulating hormone, thyroxine, thyroxine binding globulin, transferrin, tri-iodothyronine, vasoactive intestinal polypeptide, vitamins B$_6$ and B$_{12}$, staphylococcus antigens, antibodies against staphylococcus, enterotoxins, ricin, endotoxin, botulism toxin, venoms, amphetamine, methamphetamine, phenobarbital, cocaine, methadone, methaqualone, opiates (morphine, heroin), tetrahydrocannabinol (THC), phencyclidine (PCP), lysergic acid diethylamide (LSD), annabolic steroids, phenyl-butazone, amikacin, azidothymidine, benzodiazepines (diazepam and chlordiazepoxide), carbamazine, chloramphenicol, cyclosporine, digitoxin, digoxin, ethosuximide, gentamicin, imipramine, lidocaine, phenytoin, primidone, procainamide, propoxyphene, propranolol, quinidine, theophylline, tobramycin, valproic acid, trinitrotoluene, cyclonite, pentaerythritol tetranitrate, picric acid, nitroglycerin, herbicides, insecticides, polychlorinated biphenyls, polyaromatic hydrocarbons, heavy metals, glucose, F1 antigen of *Y pestis*, lethal factor or PA antigen from *B. anthracis*, and mycotoxins.

12. A displacement assay for detecting an analyte in a sample, comprising:

(a) contacting a sample which may contain said analyte with an immobilized ligand-receptor complex prepared by a process comprising:

(i) binding a labelled ligand or a labelled receptor to an immobilized receptor or an immobilized ligand, to obtain an immobilized ligand-receptor complex;

(ii) washing said immobilized ligand-receptor complex to remove any excess labelled ligand or any excess labelled receptor, to obtain a washed immobilized ligand-receptor complex;

(iii) lyophilizing said washed immobilized ligand-receptor complex, to obtain a lyophilized immobilized ligand-receptor complex, wherein said lyophilizing is carried out in the presence of a cryoprotectant; and (iv) rehydrating said lyophilized immobilized ligand-receptor complex; and (b) measuring (1) the amount of labelled ligand or labelled receptor displaced from said immobilized receptor or said immobilized ligand, or (2) the amount of labelled ligand or labelled receptor which remains bound to said immobilized receptor or said immobilized ligand.

13. The displacement assay of claim 12, wherein step (i) is carried out by binding a labelled antigen or labelled hapten to an immobilized antibody and wherein said lyophilized immobilized ligand-receptor complex is a lyophilized labelled antigen-immobilized antibody complex or a lyophilized labelled hapten-immobilized antibody complex.

14. The displacement assay claim 12, wherein said cryoprotectant is selected from the group consisting of disaccharides, polysaccharides, glycerol, proteins, surfactants, serum, buffers, polyethylene glycol, and dimethyl sulfoxide.

15. The displacement assay of claim 12, wherein said immobilized receptor or immobilized ligand is capable of specific binding to an analyte selected from the group consisting of acetylcholine receptor antibody, adenovirus antigens, antibodies against adenovirus, aldosterone, acid phosphatase, alpha-1 fetoprotein, angiotensin converting enzyme, antiDNA antibody, antimitochondrial antibody, beta-2 microglobulin, creatine kinase isoenzymes, lactate dehydrogenase isoenzymes, complement components, chlamydia antigens, antibodies against chlamydia, cortisol, C-peptide, cyclic AMP, erthyropoietin, estradiol, ferritin, folic acid, follicle stimulating hormone, gastrin, glucagon, growth hormone, histocompatibility antigens, blood group antigens A and B, haptoglobin, antibodies against hepatitis A and B, hepatitis A and B antigens, antibodies against herpes, herpes antigens, human chorionic gonadotropin, HIV antigens, antibodies against HIV, antibodies against insulin, insulin, IgA, IgD, IgE, IgG, IgM, H. influenza antigen, antibodies against the H. influenza virus, intrinsic factor antibody, Borrelia burgdorferi antigens, antibodies against Borrelia burgdoferi, luteinizing hormone, metyrapone, myoglobin, neuron-specific-enolase, p24, pancreatic polypeptide, parathyroid hormone, placental lactogen, progesterone, prolactin, prostate specific antigen, rotavirus antigens, antibodies against rotavirus, antibodies against rubella, salmonella, serotonin, somatomedin-C, $T_3$, $T_4$, testosterone, thyroglobulin, thyroid stimulating hormone, thyroxine, thyroxine binding globulin, transferrin, tri-iodothyronine, vasoactive intestinal polypeptide, vitamins $B_6$ and $B_{12}$, staphylococcus antigens, antibodies against staphylococcus, enterotoxins, ricin, endotoxin, botulism toxin, venoms, amphetamine, methamphetamine, phenobarbital, cocaine, methadone, methaqualone, opiates (morphine, heroin), tetrahydrocannabinol (THC), phencyclidine (PCP), lysergic acid diethylamide (LSD), annabolic steroids, phenyl-butazone, amikacin, azidothymidine, benzodiazepines (diazepam and chlordiazepoxide ), carbamazine, chloramphenicol, cyclosporine, digitoxin, digoxin, ethosuximide, gentamicin, imipramine, lidocaine, phenytoin, primidone, procainamide, propoxyphene, propranolol, quinidine, theophylline, tobramycin, valproic acid, trinitrotoluene, cyclonite, pentaerythritol tetranitrate, picric acid, nitroglycerin, herbicides, insecticides, polychlorinated biphenyls, polyaromatic hydrocarbons, heavy metals, glucose, F1 antigen of Y pestis, lethal factor or PA antigen from B. anthracis, and mycotoxins.

16. The displacement assay of claim 12, wherein said contacting comprises flowing said sample past said immobilized ligand-receptor complex at a flow rate allowing said analyte to displace said labelled ligand or said labelled receptor from said ligand-receptor complex under nonequilibrium conditions.

17. The displacement assay of claim 16, wherein said flowing of said sample past said immobilized ligand-receptor complex is carried out in a column.

18. The displacement assay of claim 16, wherein said flowing of said sample past said ligand-receptor complex is carried out at a flow rate between 0.1 and 2.0 milliliters per minute.

19. The displacement assay of claim 16, wherein said flowing of said sample past said ligand-receptor complex is carried out at a flow rate between 0.3 and 0.8 milliliters per minute.

20. A kit, comprising a lyophilized, dry reagent comprising: (a) a labeled ligand or labeled receptor bound to (b) a complementary receptor or a complementary ligand, wherein said complementary receptor or complementary ligand is immobilized on a solid supports, wherein said lyophilized, dry reagent is prepared by lyophilizing in the presence of a cryoprotectant.

21. The kit of claim 20, comprising a labelled antigen or labelled hapten bound to a complementary antibody, wherein said complementary antibody is immobilized on a solid support.

22. The kit of claim 20, wherein said complementary receptor or complementary ligand is capable of specific binding to an analyte selected from the group consisting of acetylcholine receptor antibody, adenovirus antigens, antibodies against adenovirus, aldosterone, acid phosphatase, alpha-1 fetoprotein, angiotensin converting enzyme, antiDNA antibody, antimitochondrial antibody, beta-2 microglobulin, creatine kinase isoenzymes, lactate dehydrogenase isoenzymes, complement components, chlamydia antigens, antibodies against chlamydia, cortisol, C-peptide, cyclic AMP, erthyropoietin, estradiol, ferritin, folic acid, follicle stimulating hormone, gastrin, glucagon, growth hormone, histocompatibility antigens, blood group antigens A and B, haptoglobin, antibodies against hepatitis A and B, hepatitis A and B antigens, antibodies against herpes, herpes antigens, human chorionic gonadotropin, HIV antigens, antibodies against HIV, antibodies against insulin, insulin, IgA, IgD, IgE, IgG, IgM, H. influenza antigen, antibodies against the H. influenza virus, intrinsic factor antibody, Borrelia burgdorferi antigens, antibodies against Borrelia burgdoferi, luteinizing hormone, metyrapone, myoglobin, neuron-specific-enolase, p24, pancreatic polypeptide, parathyroid hormone, placental lactogen, progesterone, prolactin, prostate specific antigen, rotavirus antigens, antibodies against rotavirus, antibodies against rubella, salmonella, serotonin, somatomedin-C, $T_3$, $T_4$, testosterone, thyroglobulin, thyroid stimulating hormone, thyroxine, thyroxine binding globulin, transferrin, tri-iodothyronine, vasoactive intestinal polypeptide, vitamins $B_6$ and $B_{12}$, staphylococcus antigens, antibodies against staphylococcus, enterotoxins, ricin, endotoxin, botulism toxin, venoms, amphetamine, methamphetamine, phenobarbital, cocaine, methadone, methaqualone, opiates (morphine, heroin), tetrahydrocannabinol (THC), phencyclidine (PCP), lysergic acid diethylamide (LSD), annabolic steroids, phenyl-butazone, amikacin, azidothymidine, benzodiazepines (diazepam and chlordiazepoxide), carbamazine, chloramphenicol, cyclosporine, digitoxin, digoxin, ethosuximide, gentamicin, imipramine, lidocaine, phenytoin, primidone, procainamide, propoxyphene, propranolol, quinidine, theophylline, tobramycin, valproic acid, trinitrotoluene, cyclonite, pentaerythritol tetranitrate, picric acid, nitroglycerin, herbicides, insecticides, polychlorinated biphenyls, polyaromatic hydrocarbons, heavy metals, glucose, F1 antigen of *Y pestis*, lethal factor or PA antigen from *B. anthracis*, and mycotoxins.

* * * * *